United States Patent [19]

Keffert et al.

[11] Patent Number: 5,281,819
[45] Date of Patent: Jan. 25, 1994

[54] APPARATUS FOR NONDESTRUCTIVELY DETERMINING COATING THICKNESS ON A METAL OBJECT AND ASSOCIATED METHOD

[75] Inventors: Richard G. Keffert, Penn Hills, Pa.; M. Jonell Kerkhoff, Pittsburgh, Pa.; James E. Smous, South Bend, Ind.

[73] Assignee: Aluminum Company of America, Pittsburgh, Pa.

[21] Appl. No.: 711,521

[22] Filed: Jun. 6, 1991

[51] Int. Cl.$^5$ .................. G01N 21/01; G01N 21/64; G01B 11/02

[52] U.S. Cl. .................. 250/360.1; 250/358.1; 250/359.1; 250/458.1; 250/459.1

[58] Field of Search ............... 250/358.1, 359.1, 360.1, 250/458.1, 459.1, 461.1, 372; 209/538, 576, 577, 587; 269/287, 254 R; 356/428, 381; 279/151, 906

[56] References Cited

U.S. PATENT DOCUMENTS

| | | |
|---|---|---|
| 694,413 | 3/1902 | Pennington .................. 269/287 |
| 698,057 | 4/1902 | Miller et al. .................. 269/287 |
| 2,735,017 | 2/1956 | Beard et al. .................. 250/372 |
| 3,150,266 | 9/1964 | Mathias .................. 356/428 |
| 3,751,643 | 8/1973 | Dill et al. . |
| 3,767,920 | 10/1973 | Kido et al. .................. 250/359.1 |
| 3,922,213 | 11/1975 | Smith et al. . |
| 3,994,586 | 11/1976 | Sharkins et al. .................. 250/341 X |
| 4,029,958 | 6/1977 | Wright .................. 209/587 |
| 4,094,760 | 6/1978 | Smith et al. . |
| 4,129,781 | 12/1978 | Doyle .................. 250/341 |
| 4,210,507 | 7/1980 | Davidson et al. . |
| 4,400,251 | 8/1983 | Heffner et al. . |
| 4,437,010 | 3/1984 | Scheie et al. . |
| 4,460,274 | 7/1984 | Schumann et al. . |
| 4,544,475 | 10/1985 | Heffner et al. . |
| 4,634,291 | 1/1987 | Bantel et al. . |
| 4,651,010 | 3/1987 | Javan . |
| 4,656,358 | 4/1987 | Divens et al. . |
| 4,675,529 | 6/1987 | Kushida .................. 250/458.1 |
| 4,676,881 | 6/1987 | Davidson . |
| 4,807,421 | 2/1989 | Araki et al. .................. 269/287 |
| 4,841,156 | 6/1989 | May et al. .................. 250/461.1 |
| 4,894,547 | 1/1990 | Leffell et al. .................. 250/461.1 |
| 5,001,353 | 3/1991 | Odake et al. .................. 250/372 |

FOREIGN PATENT DOCUMENTS

| | | | |
|---|---|---|---|
| 2155625 | 9/1985 | European Pat. Off. ............ 356/428 |
| 2907620 | 8/1980 | Fed. Rep. of Germany . |
| 63760 | 11/1982 | Fed. Rep. of Germany ...... 356/428 |
| 57-108704 | 7/1982 | Japan .................. 250/358.1 |
| 58-10638 | 1/1983 | Japan .................. 250/358.1 |
| 60-129646 | 7/1985 | Japan .................. 356/381 |

Primary Examiner—Constantine Hannaher
Assistant Examiner—Edward J. Glick
Attorney, Agent, or Firm—Arnold B. Silverman; William J. O'Rourke, Jr.

[57] ABSTRACT

Apparatus and an associated method for nondestructively determining the thickness of a coating on a metal surface, such as the interior of a can. An object securing device holds the object being inspected. The inspection device includes a probe. Positioning apparatus is employed to permit insertion of the probe into inspecting relationship which in the case of a can would involve partial insertion of the probe into the can. A first section is inspected and sequentially through relative rotational and/or translational movement of the object being inspected additional portions of the object such as can ends may be inspected. A light beam is caused to impinge upon the section of the object being inspected and returned fluorescent light received by a detector positioned within the probe cooperates with processing means to determine the coating thickness. The system permits accurate determinations of coating thickness even when the metal surface has irregularities. The system may be employed on metal sheet including moving metal sheet. The probe may include mirrors and fiberoptic components. A suitable lens for focusing the returned light and a filter for excluding extraneous returned light from the detector preferably are employed. A container holder is also provided.

40 Claims, 5 Drawing Sheets

EPOXY FLOURESENCE FROM CAN INTERIOR

APPARATUS FOR NONDESTRUCTIVELY DETERMINING COATING THICKNESS ON A METAL OBJECT AND ASSOCIATED METHOD

BACKGROUND OF THE INVENTION

1. Field of the Invention

This invention relates to apparatus and an associated method for nondestructively determining the coating thickness on a metal surface, such as the interior of a metal can or a metal sheet.

2. Description of the Prior Art

It has been known to coat curved metal surfaces such as the interiors of cans in order to resist potentially damaging contact between the metal surface and materials which will be contained within or come into contact with the metal object. For example, in connection with aluminum cans used for food products, in order to resist undesired corrosive attack by the food products on the metal, or undesired chemical reactions which could alter the taste of the food products, the can interior is generally coated with an organic coating. It is important that the coating have the desired thickness in order to avoid providing an inadequate barrier due to an unduly thin coating, or interference with can forming techniques due to a coating which is of an excessive thickness. On metal sheet lubricating oil coatings may be present.

A number of means of coating such can interiors have been known, including various electrocoating processes. See generally U.S. Pat. Nos. 3,922,213, 4,094,760, 4,210,507, 4,400,251, 4,544,475 and 4,676,881.

It is has also been known to inspect coating thickness on can interiors by employing destructive testing techniques. These techniques involve periodically removing a sample can from the line and cutting it into pieces with coating thicknesses being measured on the sections. In connection with such destructive testing, various known means such as carbon analysis may be employed to ascertain coating thickness as a function of location within the can. Among the problems with destructive testing are the fact that destructive testing of this type is very time-consuming. By the time the results are available, a great number of containers may have been made with coated portions that are not within specifications. Also, even if the can passes the test, the destructive testing involved destruction of a good quality product.

U.S. Pat. No. 3,751,643 discloses the use of an spectrophotometer in measuring dielectric film thickness. This nondestructive-method involves monitoring variations in the interference effect caused by the difference in light reflected from the film and from the substrate are monitored. Computer means are employed to assist with computations.

It has been known to employ laser energy in measuring the thickness of a coating by monitoring radiant energy as compared with standard thickness specimens. See U.S. Pat. No. 4,634,291.

U.S. Pat. No. 4,656,358 discloses the use of ultraviolet laser beams in the nondestructive, noncontacting measurement of dimensions of sample wafers. It discloses the use of returning light solely from the spot on which the ultraviolet light impinges and the use of fluorescence created within the material being examined.

It has also been know to add materials to a coating in order to enhance fluorescence responsive to imposing a laser beam thereon. See U.S. Pat. Nos. 4,437,010, 4,460,274, 4,651,010 and German Patent 29 07 620.

U.S. Pat. No. 4,841,156 discloses the measurement of thickness of films employing the concept that the fluorescent light is proportional to a film thickness. The fluorescent light is filtered before being received by a photodetector which converts the light into an electrical signal. The system employees two signals and the use of a divider to compare the signals.

In spite of the foregoing known systems, there remains a very real and substantial need for a non-destructive, non-contacting system for accurately measuring the thickness of a relatively thin coating on a curved metal object, such as a metal can.

SUMMARY OF THE INVENTION

The present invention has met the hereinbefore described need. In one embodiment of the present invention a curved surface of a metal object is supported in or on an object securing means. Inspection means which includes a probe for inspecting the curved surface are provided. Positioning means serve to position the probe adjacent to the curved surface to be inspected. A first section of the curved surface is inspected by the probe and subsequently through establishing relative rotational and/or translational movement additional sections are inspected. The entire surface of the object may be inspected if desired. In the case of the inspection of a cylindrical metal can, for example, this inspection may include the entire interior surface of the can including the bottom surface.

In another embodiment the invention may be employed to measure coating thickness on a metal sheet.

The probe has an opening which both transmits the beam of light to the section being inspected and receives returned light for evaluation. The probe preferably contains the detector means which are operatively associated with electrical processing means which may take the form of a computer. In operation, a light beam is transmitted to the section of the coated metal surface being inspected and light returns to the probe from such section. In a preferred approach optical fiber means transmits the light to the section. A mirror and a focusing lens is preferably employed to focus the light returning from the section to make sure that it impinges upon the desired portion of the detector means. Filter means are preferably interposed between the lens and the detector means to filter stray light which did not originate as fluorescence within the section being inspected.

The detector means preferably has means for eliminating distortions in the thickness reading which might occur due to surface irregularities in the metal object surface whose coating has been inspected.

It is an object of the present invention to provide non-destructive testing means for rapid and accurate determination of the thickness of a coating on a metal surface.

It is another object of the present invention to provide such a system which may be employed to inspect all or substantially all of the interior coating of metal cans to be used for beverages or food.

It is a further object of the present invention to provide a compact system of this type which has a probe of sufficiently small size as to be introduced into the can interior.

It is a further object of this invention to provide such a system that may be employed to measure coating thickness on a metal sheet.

It is a further object of the present invention to provide such a system for use in either a sampling mode which samples containers periodically for inspection or in a complete manner to inspect all containers.

It is a further object of the invention to provide such a system which can rapidly and economically effect such inspection.

It is another object of the present invention to permit such a system to be incorporated in a can fabricating line such that servo means may be employed to adjust the coating system in the event that a departure from desired standards has been found to exist.

These and other objects of the invention will be more fully understood due to the following detailed description of the invention on reference to illustrations appended hereto.

BRIEF DESCRIPTION OF THE DRAWING

FIG. 1 is a perspective view of a preferred form of can holder of the present invention.

DESCRIPTION OF THE PREFERRED EMBODIMENTS

Figure 1:
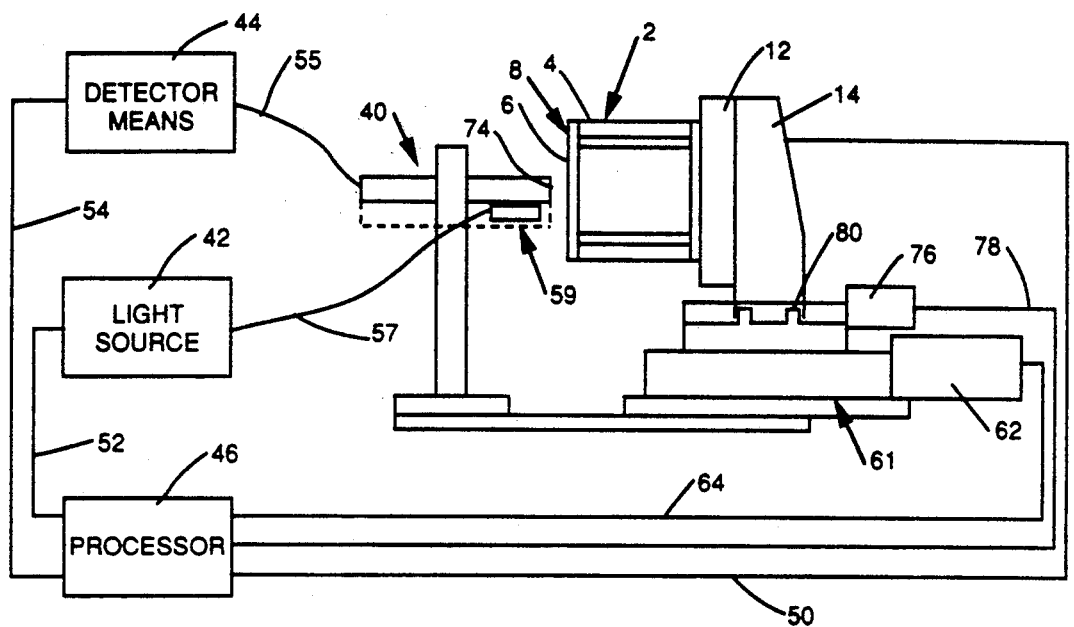
FIG. 1 is a schematic illustration of one form of the inspecting apparatus of the present invention.
Figure 2:
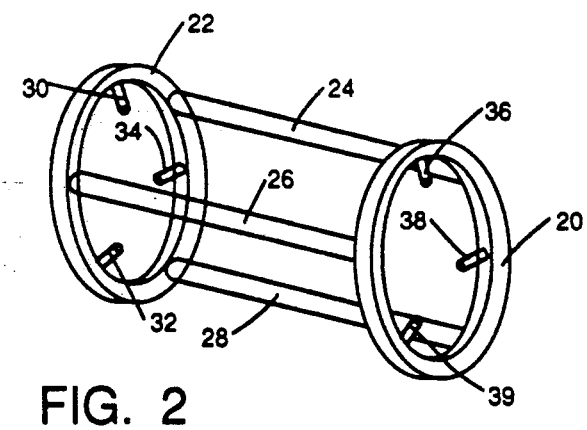

While it will be appreciated that the present invention is applicable to the nondestructive inspection of coating thicknesses on a number of metal surfaces, a principal application is the use in connection with the measurement of relatively thin coatings which may be on the order of about 100 to 500 microinch on the interior wall or end of a metal can such as an aluminum can having a wall thickness of about 8 to 12 mils.

As will become apparent from the disclosure which follows the present invention employs a light beam, such as argon laser beam, for example, of a first wavelength to create fluorescent light of a different wavelength in the coating. The fluorescence is directly related to the coating thickness. The fluorescence capability may be inherent in the coating material such as in epoxy coatings. In respect of some materials such as certain oils a fluorescent tag may be added to create the desired level of fluorescence. For example, in determining the thickness of a dioctyl sebacate oil coating, riboflavin tetrabutyrate may be employed as a fluorescent tag.

Referring now more specifically to FIGS. 1 through 4, there is shown a preferred form of apparatus of the present invention. The article to be inspected, which in the form shown is a generally cylindrical empty aluminum can 2 having an annular sidewall 4, an open end 6 and a closed end which may be integrally formed is positioned with its longitudinal axis generally horizontally oriented. The can 2 is secured within can holder 8 which is fixedly secured to rotary support 12 which in turn is mounted in housing 14. The closed can end (not shown) is in intimate contact with rotary support 12. A preferred form of can holder 8 is showing in FIG. 2. A substantially rigid frame consisting of a pair of spaced circular rings 20, 22 are of equal diameter and are connected by 3 circumferentially equally spaced struts, 24, 26, 28. The outer surface of one ring 20, 22 will be fixedly secured to rotary support 12. In order to facilitate ease of insertion and withdrawal of cans while effecting intimate engagement during inspection each ring has a plurality of spring biased radially inwardly projection can engaging fingers 30, 32, 34, 36, 38, 39. These fingers may be mounted on set screws to facilitate use of the holder with cans of different diameter. The interior surfaces of rings 20, 22 are of greater diameter than the exterior diameter of the cans.

It will be appreciated that the adjacent radially spring biased fingers on a rings 20, 22 are circumferentially spaced from each other.

The inspection means includes a probe 40 which may physically contain or be operatively associated with a light source 42 and detector means 44. Electronic processing means, which preferably take the form of a digital processor 46, is connected with stepper motor 18 (FIG. 4) by lead 50, light source 42 by lead 52 and detector means 44 by means of lead 54. The detector means 44 is connected to the probe 40 by electrical lead 55. The light source 42 emits laser light through optical fiber 57 to the lens-mirror assembly 59 which will be described hereinafter.

In effecting inspection it is preferred that the can move with respect to a stationary probe. The can sidewall moves in a generally axial direction adjacent to the probe which inspects that portion of the sidewall in a generally continuous manner at a plurality of points as the can moves by. The can end is then inspected in a generally continuous manner by establishing movement of the can in a direction perpendicular to the can axis in order to inspect a first radial portion of the can end between its inspected sidewall portion radially inwardly to the center of the end. The can and probe 40 are subjected to relative axial separating movement to place the probe 40 in starting position as by the can retracing its relative movement with respect to the probe 40. The can is then rotated about its axis and the cycle of inspection is repeated with different portions of the sidewall and end being inspected. The probe is preferably positions about 5 to 7 mm from the portion of the can that it is inspecting. For example, the can might be rotated about 60 degrees between inspection cycles, and may inspect at 170 equally spaced longitudinal locations on the sidewall of a four inch can body with each pass.

Figure 3:
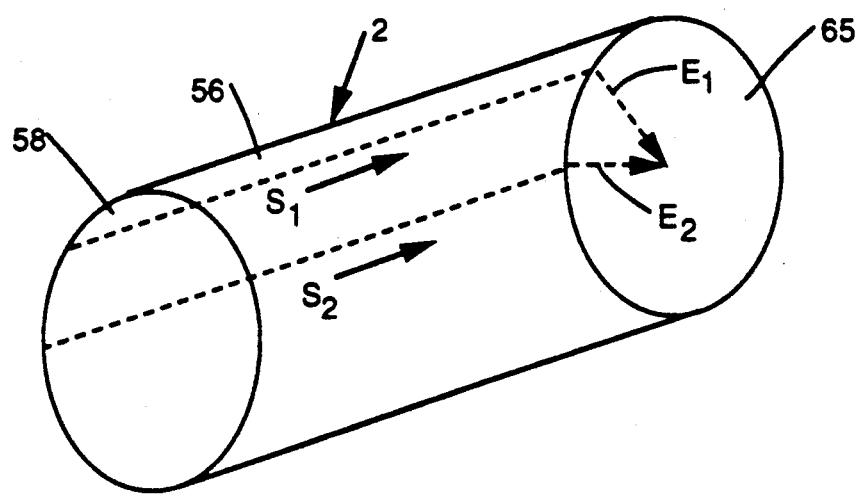
FIG. 3 is a schematic illustration of a can inspection sequence.
Figure 4:
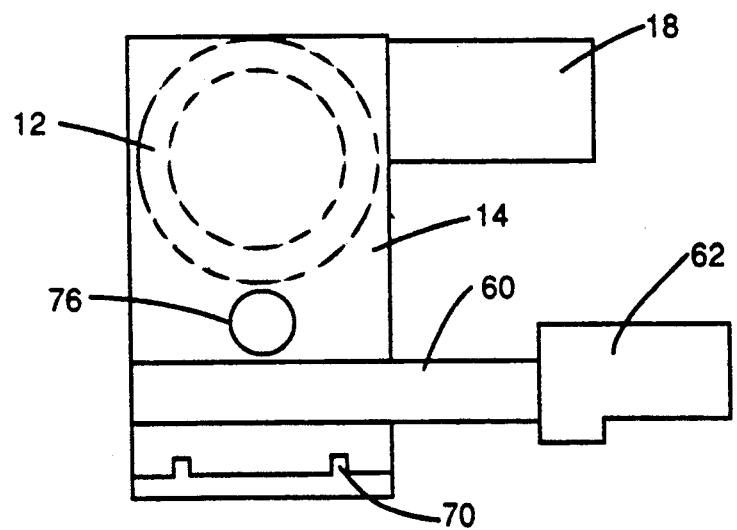
FIG. 4 is an end elevational illustration of a portion of the apparatus of FIG. 1.

As shown in FIG. 3, the can 2 has a sidewall 56, an open end 58 and a closed end 65. The cycle of inspection described involves initial inspection of sidewall portion $S_1$ followed by radially inwardly directed end inspection on end portion $E_1$. After withdrawal of the can 2 from probe 40 and return of the probe 40 to the starting position, the can 2 is rotated axially to the next starting position after which inspection of sidewall portion $S_2$ and end portion $E_2$ are effected. Subsequent cycles may be effected in the same manner.

It will be appreciated that in the preferred embodiments of the present invention the container 2 and probe 40 will be subjected to relative movement in three ways. Translational movement in an axial direction and in a direction perpendicular to the axis will facilitate inspection of a sidewall portion and an end portion. Relative rotational movement will permit inspection of other portions of the container interior. The means for effecting the three degrees of motion will be well known to those skilled in the art. Suitable equipment for accomplishing these objectives is available from Daedal, Inc. of Harrison City, Pa. In the form shown in FIGS. 1 and 4, a stepping motor 18 has a rotary output shaft (not shown) engaging rotary support 12 through a suitable gearing (not shown). Processor 46 will emit signals to motor 18 by lead 64 to control rotation of rotary support 12. The housing 14 is mounted on a movable platform 61 which under the influence of motor 62 which is connected to processor 46 by lead 64, translates housing 14. In effecting translation of the can 2 to the initial testing position the platform 61 is moved in an axial direction toward the probe 40 until the probe's leading end 74 enters the can 2 to the desired extent. In effecting inspection of sidewall sections such as $S_1$ and $S_2$ in FIG. 3 translation of the can 2 in a generally axial direction will be effected by moving platform 61 which supports housing 14 along track 70 under the influence of motor 62. Similarly motor 76 which is connected to processor 46 by lead 78 effects translational movement of housing 14 in a direction transverse to the axis of the can on track 80.

By way of general summary of the operation of the apparatus of the present invention, the probe 40 will be inserted partially into the interior of can 2 through relative movement therebetween. A light beam emitted from the probe 40 will impinge upon a first section of the can 2 which is to be inspected. Responsive fluorescent light coming off of that section of the can interior will be directed toward the detector means 44 which will convert the light into a corresponding electrical signal, which by lead 54 will be introduced into the processor or computer 46. Thereafter all the sections of the container desired to be inspected have been inspected, the resultant information may be displayed, stored or employed to activate a can reject mechanism. It may also be employed to activate or adjust other equipment to provide a servosignal that adjusts upstream equipment, such as coating equipment, for example.

Figure 5:
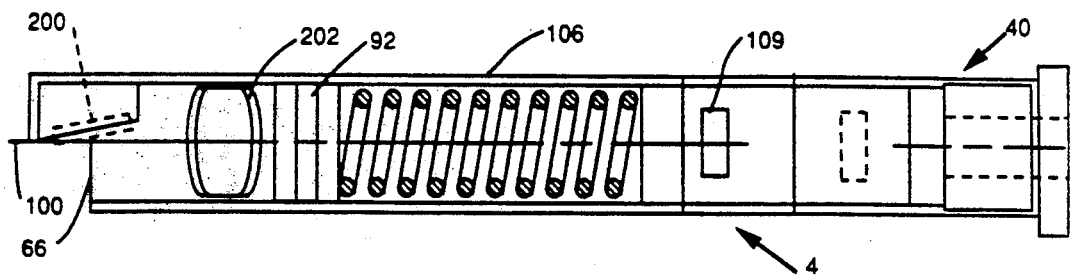
FIG. 5 is a cross-sectional elevational view of a form of the probe of the invention.
Figure 6:
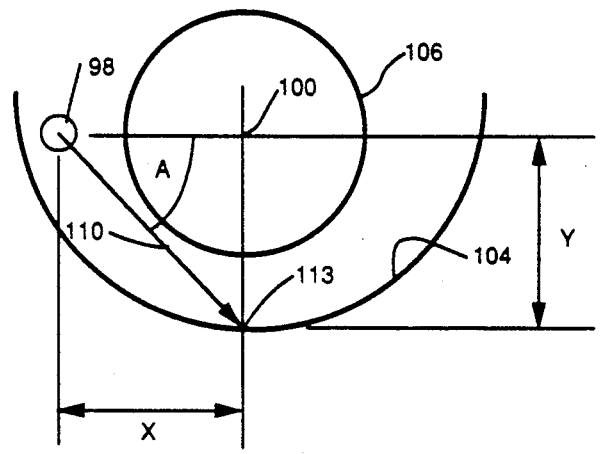
FIG. 6 is a schematic illustration of the inspection of the interior of a sidewall of a can.
Figure 7:
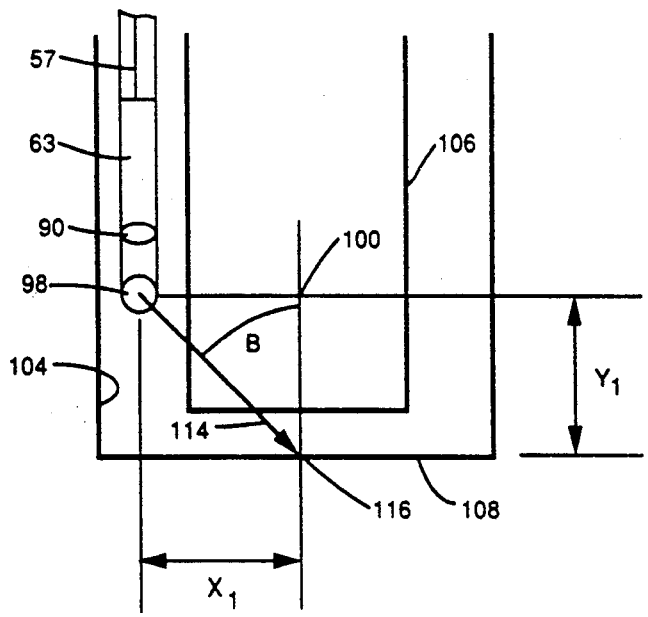
FIG. 7 is a schematic illustration of the inspection of the interior of the can end.

Referring to FIGS. 5 and 7, there is shown a preferred form of probe 40 of the present invention. As stated hereinbefore, the probe 40 may physically contain or be operatively associated with a light source 42 and detector means 44. In the form illustrated in FIGS. 5 through 7, the light source is disposed externally of the probe and the detector means within the probe.

The probe 40 is preferably tubular and has a generally circular cross-sectional configuration. It has a metal housing 106. At one end of the housing 106, a light receiving opening 66 is provided. The opening is stepped to facilitate receipt of light. In a preferred embodiment, an optical fiber 57 which is connected to laser 42 (FIG. 1) is employed to deliver light to the probe 40. The light passes through metal ferrule 63 and ball lens 90 which focuses the beam of light on angularly disposed mirror 98 which is preferably disposed at an angle of 27° to the longitudinal axis 100 of the probe 40. The ball lens 90 and mirror 98 are fixedly secured to ferrule 63. Ferrule 63 is axially rotatably mounted by securement to the sensor housing 106, for example, in a manner well known to those skilled in the art. For example, the ferrule 61 may be rotatably secured within a holder secured to the exterior of the sensor housing 106 with a set screw being employed to secure the ferrule 63 in the desired position. The mirror 98 directs the light beam onto the metal coated sector being inspected. The probe 40 has a sensor housing 106 which contains mirror 200 for receiving light from the coating. The sensor head 106 also contains ball lens 202 and photodiode 109 on which the returning light impinging on mirror 200 is focused by lens 202 after passing through filter 92 to eliminate stray light.

Referring to FIG. 6 there is shown the can inner surface 104 and the probe sensor housing 106 and mirror 98 from which light beam 110 is directed to section 113 of the can inner surface 104. The light beam 110 forms an angle A of about 45° with a plane passing through the center of the mirror 98 and the longitudinal axis 100 of the probe 40. It is preferred that the distance X between the mirror center and axis be about 19 to 21 mm and that the distance Y between the axis 100 and section 113 be equal to the distance X.

FIG. 7 shows a view perpendicular to that of FIG. 6 with the can end 108 being inspected. The system functions essentially as described with respect to FIG. 6. The mirror 98 is positioned by axial rotation of ferrule 63 to cause light reflecting off mirror 98 to impinge on section 116. The mirror 98 is positioned at distance X as in FIG. 6 as this is a fixed relationship within the probe 40. Angle B, which is the angle between a plane passing through the central axis 100 and the center of sector 116 and the light beam 114, is preferably about 45 degrees. The distance $Y_1$ is preferably equal to distance $X_1$. After section 116 has been inspected, transverse translational movement of the can is effected to permit inspection of the next can bottom section.

The light impinging on the coating will have a wavelength different from and generally of shorter wavelength than the responsive fluorescent light.

In both the inspection modes of FIGS. 6 and 7 with reference to FIG. 7, fluorescent light returning from the coating of can 104 is directed by mirror 200 (FIG. 5) through ball lens 202 to detector means 109, which is preferably a photodetector. Filter means 92 are interposed on the line of returning light travel which, in the form shown, is the axis 100 of probe 40 in front of the detector means 109. This filter means 92 filters stray light which could interfere with the processing of the returned light. The detector means 109 converts the received light to a corresponding electrical signal which is delivered to computer means 46 by lead 54 for further processing. In effecting this processing, the detector means cooperates with the computer means 46 to eliminate distortions in the light received by the detector means 109 due to surface irregularities on the interior of the can.

The system inherently determines where the metal surface is and converts the responsive fluorescent light which is proportional to the coating thickness in the specific section to a thickness value.

Alternate approaches would be to use measurements of absorption or reflectance of the light at the same wavelength within the section being inspected. This is to be distinguished from the preferred use of fluorescence wherein the absorption wavelength differs from the fluorescence wavelength. In such cases, the light employed may be within the ultraviolet, visible or infrared spectrum.

The computer determined values will preferably be compared with the standard specifications and a determination made as to whether the individual sections meet specifications. If they do not, the computer 46 will provide information regarding what section or sections depart from specifications. This information may then be printed out in hard copy as in a three dimensional relief plot or a numerical chart. The information may also be employed to feed through a servomechanism to the coating equipment to make appropriate adjustments therein automatically. The system can be used either as a sampling system, one which periodically removes a container from the line for purposes of sampling or all containers can be sampled as the testing is not destructive. The system could also be employed to activate a reject mechanism which would discard cans not meeting specifications.

The probe 40 preferably has an outer diameter which is less than the internal diameter of the can being inspected. The probe may have an outer diameter of 1 to 1¼ inches, for example. The overall length of the probe may be about 4 to 8 inches and the internal diameter may be about ½ to 1 inch.

Figure 8:
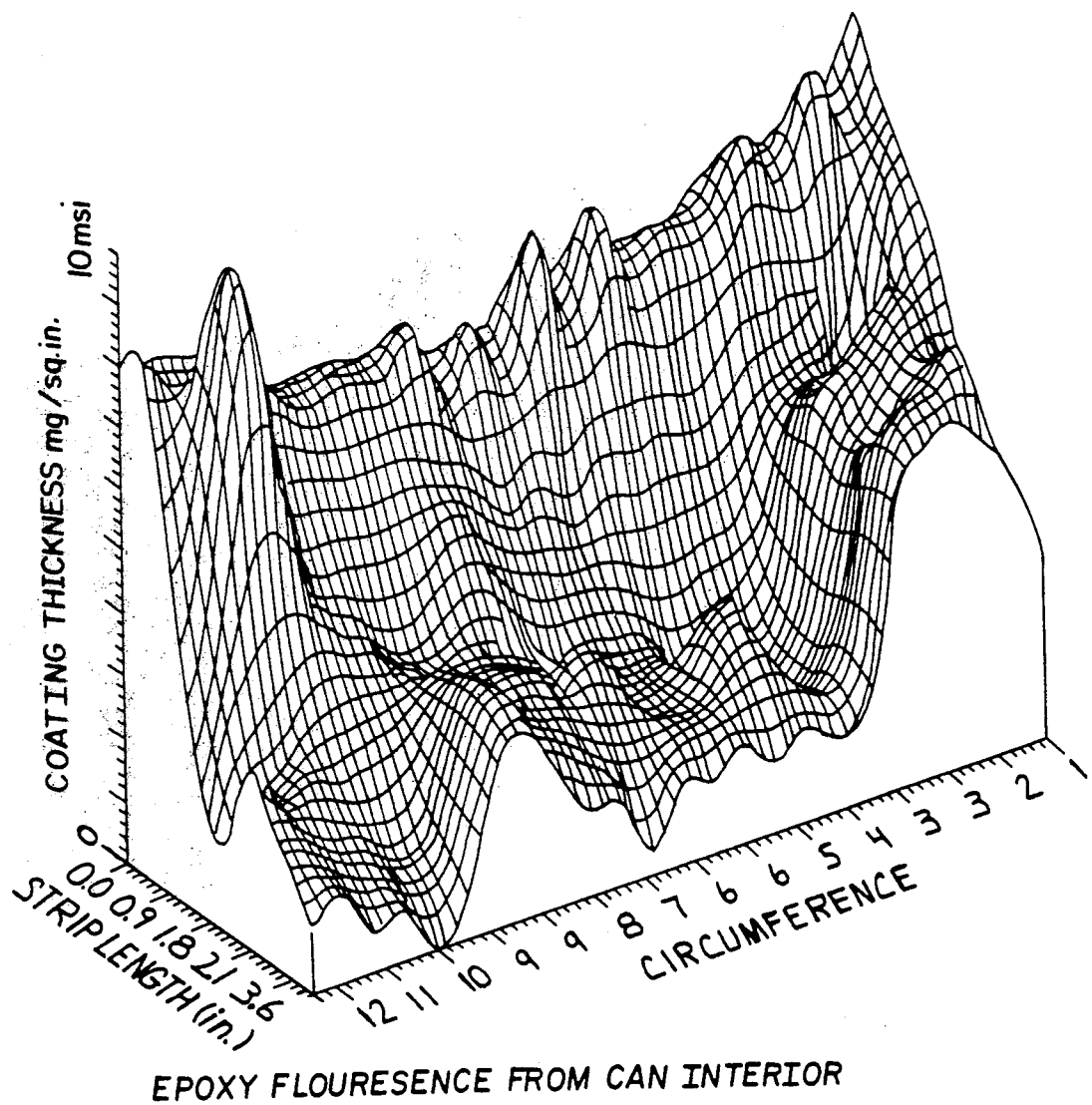
FIG. 8 is a three dimensional profile produced by the system of the present invention.

Referring to FIG. 8 there is shown a three dimensional plot generated by inspecting a can interior having an epoxy coating. The plot shows variations in coating thickness in $mg/in^2$ as related to the axial and circumferential position of the can. This plotting is provided by the computer 46 which records the axial and rotational position of each increment of data as to the sidewall. FIG. 8 shows that the coating in the can inspected was thicker at the closed end of the can. Also, the coating has unacceptably thin areas at about sections 7 and 10. The processor 46 would be programmed to provide the desired coating thickness standards and acceptance or rejection of cans based upon such standards.

Figure 9:
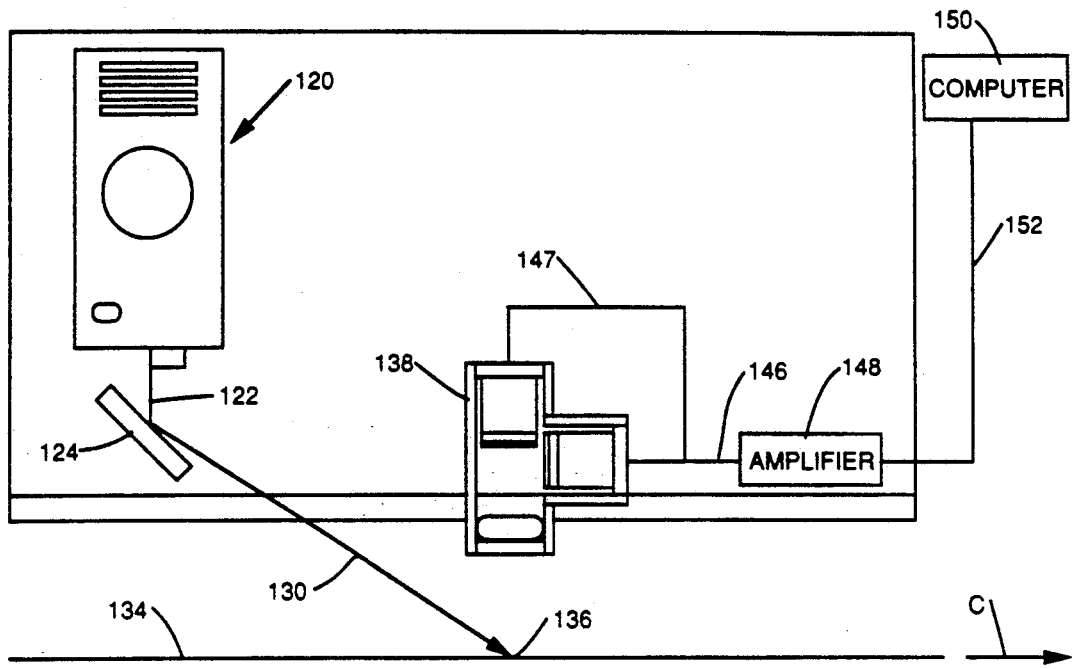
FIG. 9 is a schematic illustration of a form of the invention employed in measuring the coating thickness on a flat sheet.

Referring to FIG. 9 there is shown a modified embodiment of the invention that employs two detectors. An argon laser 120 emits a light beam 122 to mirror 124 which causes the reflecting light beam 130 to impinge on aluminum sheet 134 at section 136. The coating fluorescent light passes into detector housing 138. The detector converts the light into corresponding electrical signals. The responsive electrical signals pass on lines 146, 147 to amplifier 148. The amplified signal passes to computer 150 by lead 152 for processing. During such inspection the sheet may be moving as in the direction indicated by arrow C between a supply coil and a take up coil (not shown).

Figure 10:
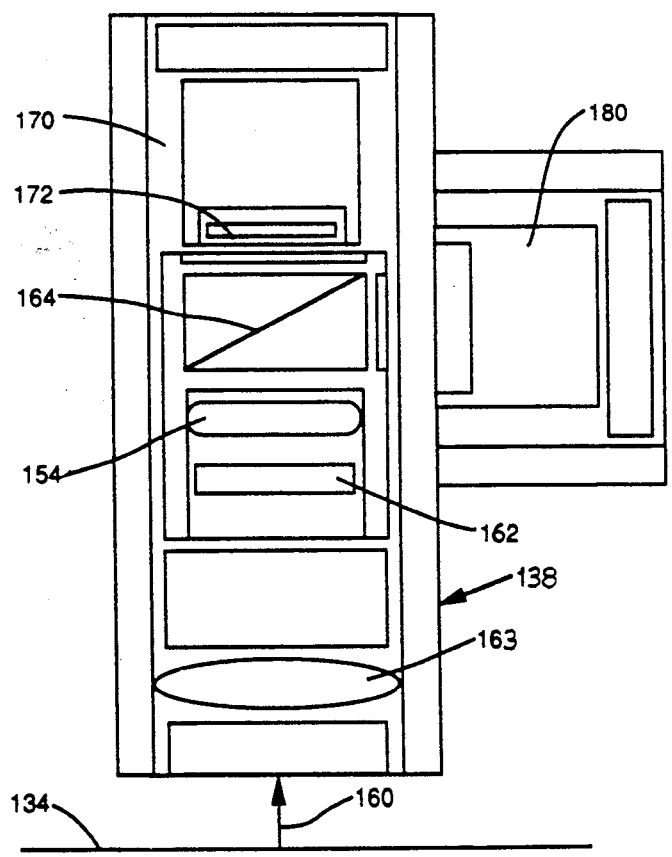
FIG. 10 is a cross-sectional illustration of a probe having two detectors.

Referring to FIG. 10 details of the detector housing 138 will be considered. The fluorescent light beam 160 emerges from the coating, enters the detector housing 138 and passes through collecting lens 163 from which it passes through filter means 162 and then through field lens 154. Prism 164 splits the light with one part going to detector 170 after passing through notch filter 172. The other portion goes to detector 180. One detector 180 measures all of the light in beam 160, e.g. fluorescence, ambient and scatter lighting, while the other measures only ambient and scatter lighting. The difference amplifier 148 receives input from each detector 170, 180 over leads 146, 147 and outputs the difference which is proportional to coating thickness.

This embodiment may be employed to measure the coating thickness of a rapidly moving aluminum sheet. For example the thickness of a tagged dioctyl sebacate coating may be measured.

If desired, a series of systems such as shown in FIGS. 9 and 10 may be positioned in transversely spaced relationship across the width of the strip and simultaneously measure several sections of the sheet. Within any longitudinal sheet section measurement will preferably be made on a continuous basis. If desired it may be employed intermittently to measure discrete longitudinal portions within such transverse sections.

EXAMPLE 1

In order to refine the disclosure of the invention an example of the use of the embodiment illustrated in FIGS. 1 through 6 will be provided. A cylindrical aluminum food can composed of alloy 3004 H-19 temper having an integrally formed can end has a length of 4 inches and a wall thickness of 10 mils. An interior epoxy coating of a thickness of 300 microinches is secured to the sidewall and end. A can is moved with respect to the probe in an axial closing direction with the probe mirror positioned about 6 mm from one sidewall. As the can moves the probe 40 inspects the sidewall until the probe is positioned about 6 mm from the closed can end. The can is then moved to cause the probe to translate relatively radially in a first path toward the can center, while inspecting the can end. The can then retraces its entry inspection path in reverse to return to the starting position. In the preferred embodiment, no inspection occurs during such retracing, however, such inspection could be effected, if desired. The can 12 is then rotated axially 60 degrees and the cycle of sidewall and end inspection is repeated. This sequence is repeated until the desired amount of inspection of the sidewalls and can end has been inspected. The probe will take 170 equally spaced thickness readings as it moves axially with respect to a sidewall in one pass. The impinging light from an argon laser has a wavelength of 457 nm at an intensity of 5 mw. The fluorescent light created responsive to the impinging light has a wavelength of 550 nm. The detector may be a 1 cm diameter photodiode operating in the current mode. The fluorescent light intensity is proportional to the intensity of the impinging light and the coating thickness. The computer is readily calibrated to determine the coating thickness at a given excitation light intensity and coating material. The fluorescence and scattered excitation light from the coating sector being inspected reflects off the angled mirror 200 at 22.5 degrees with respect to the longitudinal axis 100 toward the lens 202 which has a focal length of 40.3 mm. A low pass filter with a cutoff wavelength at 470 nm is disposed behind the lens to attenuate the scattered excitation light. Disposed adjacent thereto is a 25 nm bandpass filter centered on a wavelength of 550 nm to further attenuate the excitation light and reject thermal energy scattered from the sample area.

It is preferred to inspect such containers at a constant temperature which may be about 72° F. Regardless of what temperature is selected, it is preferred to control the temperature within ±1° F. or to compensate for temperature fluctuation.

EXAMPLE 2

An example of the embodiment of FIGS. 9 and 10 will be considered. Aluminum rigid container sheet comprised of alloy 5182 of a thickness of 10 mils is moving by the detector housing 138 at up to about 2000 feet per minute. The sheet is coated with dioctyl sebacate oil containing a riboflavin tetrabutyrate tag. The coating is present in a thickness of 5-20 nanometers (0.5-2 mg/ft$^2$). The inspection will cover the longitudinal coating section underlying the detector housing 138. If desired a plurality of transversely spaced inspection units may be employed to inspect several portions of the sheet simultaneously.

It will be appreciated that the present invention has provided an efficient, rapid system for accurate measurement of relatively thin coatings on metal objects such as the interior coatings on metal cans or coating on metal sheet. This is accomplished in a manner that eliminates distortions due to surface irregularities of the metal.

While for simplicity of disclosure herein, the description has centered around a preferred use in connection with the inspection of interior coatings of metal cans or metal sheet, it will be appreciated that the invention is not so limited and that it is capable of inspecting a large variety of coatings on metal objects.

It will be appreciated that the invention may be employed in both metal food and beverage cans as well as other containers made of rigid packaging sheet.

Whereas particular embodiments of the invention have been described herein for purposes of illustration. It will be evident to those skilled in the art that numerous variations of the details may be made without departing from the invention as set forth in the appended claims.

We claim:

1. Apparatus for nondestructively determining the thickness of a coating on an interior coated surface of a metal can having a cylindrical wall and end wall comprising:
   object securing means for supporting said can during inspection,
   probe means for inspecting the interior coated surface of the cylindrical wall and end wall of the supported can,
   positioning means for effecting relative translational movement of said can and said probe means to position said probe means within said can adjacent to the interior coated surface thereof,
   said probe means having light source means for causing a light beam to impinge on a first section of the interior coated surface of said can,
   detector means for detecting light from said first section of said interior coated surface responsive to the impinging light beam on said coating of said first section,
   processing means for receiving signals from said detector means and for determining the coating thickness on said first section of said can interior coated surface, and
   said positioning means having means for sequentially effecting relative movement between said probe means and said interior coated surface to permit inspection of other sections of said can interior coated surface, whereby the thickness of the coating on the interior cylindrical wall and end wall may be determined at a plurality of locations.

2. The apparatus of claim 1 including:
   said detector means having means for receiving fluorescent light from said interior coated surface.

3. The apparatus of claim 2 including:
   said object securing means being can retaining means for securing a generally cylindrical metal can having an open end generally facing said probe means, and
   said probe means being positioned to be generally aligned with said open can end and having a lesser outer diameter than the interior diameter of said can, whereby said probe means can be at least partially received in the can interior for inspection thereof.

4. The apparatus of claim 3, including:
   said probe means having a light discharging and receiving opening, and
   said positioning means positioning said light discharging and receiving opening to be positioned within said can.

5. The apparatus of claim 4 including:
   said positioning means having means for progressively effecting relative rotational movement and relative axial translational movement between said can and said probe means to cause predetermined sections of said can interior coated surface to be inspected.

6. The apparatus of claim 5 including:
   said processing means having means for eliminating metal surface irregularity induced variations, whereby accurate coating thickness determinations are made for can interiors having surface irregularities.

7. The apparatus of claim 5 including:
   said light source means being a laser means, and said detector means having photodiode means for detecting said fluorescent light.

8. The apparatus of claim 5 including:
   said light source means being a source of visible light or infrared light, and
   said processor means having means for determining coating thickness by fluorescence induced in said coating by said impinging light beam.

9. The apparatus of claim 5 including:
   said positioning means having means for effecting relative translational movement of said can and said probe means in a direction generally perpendicular to the longitudinal axis of said can.

10. The apparatus of claim 9 including:
    said probe means having said light discharging and receiving opening disposed at an end thereof.

11. The apparatus of claim 9 including:
    said positioning means for effecting said generally perpendicular translational movement to allow inspection of the end wall of said can interior coated surface.

12. The apparatus of claim 9 including:
    light receiving means for receiving from said can interior coated surface light responsive to the impinging light beam and delivering at least a portion of the received light to said detector means.

13. The apparatus of claim 12 including:
    said detector means being disposed within said probe means.

14. The apparatus of claim 13 including:
    said positioning means having motor means for effecting incremental rotation of said can relative to said probe means.

15. The apparatus of claim 12 including:
    said light receiving means having first mirror means for directing said at least a portion of said received light toward said detector means.

16. The apparatus of claim 15 including:
    said receiving means having filter means disposed between said first mirror means and said detector means for filtering light emanating from sources other than the fluorescent light from the can interior coated surface being inspected.

17. The apparatus of claim 16 including:
said light receiving means having a first lens means for focusing said at least a portion of said received light on said detector means.

18. The apparatus of claim 17 including:
said probe means having optical fiber means, second mirror means and second lens means for delivering light to the section of said can interior coated surface being inspected.

19. The apparatus of claim 18 including:
said probe means having a housing composed with metal, and
said housing having an exterior diameter of about 1 to 1¼ inches and a length of about 4 to 8 inches.

20. The apparatus of claim 18 including:
said probe means having a probe housing,
said detector means, said first mirror means and said first lens means being disposed within said housing, and
said optical fiber means, second mirror means and second lens means disposed exteriorly of said probe housing.

21. The apparatus of claim 20 including:
said second lens means and said second mirror means being rotatably mounted to said probe housing.

22. The apparatus of claim 1 including:
said object securing means being an elongate can holder having a plurality of radially spring biased can engaging fingers secured to a pair of relatively spaced end rings,
longitudinal struts connecting said end rings, and
said fingers being circumferentially spaced from adjacent said fingers on the same said ring.

23. Apparatus for nondestructively determine the thickness of a coating on the surface of a metal object comprising:
light source means for causing a light beam to impinge on a first section of the coated metal surface,
detection means for receiving light from said coated metal surface responsive to said light beam and converting said light into a corresponding electrical signal,
said detection means having means for receiving fluorescent light from said coated metal surface,
said detection means having a first detector for receiving fluorescent light, ambient light and scatter light and a second detector for receiving solely ambient light and scatter light,
processing means for receiving said electrical signal and determining the thickness of said coating therefrom,
said processing means having means for subtracting an output signal of said second detector from an output signal of said first detector to produce a signal corresponding to coating thickness,
positioning means for effecting relative movement between said detection means and said metal object to permit sequential inspection of a plurality of sections of said coated metal object, and
said positioning means having means for moving said coated metal object by said detection means.

24. The apparatus of claim 23 including:
said processing means having a computer for receiving said signal corresponding to coating thickness and determining the coating thickness.

25. Apparatus for nondestructively determining the thickness of a coating on the surface of a metal object comprising:
light source means for causing a light beam to impinge on a first section of the coated metal surface,
detection means for receiving fluorescent light from said coated metal surface responsive to said light beam and converting said light into a corresponding electrical signal,
said detection means having a first detector and a second detector,
processing means for receiving said electrical signal and determining the thickness of said coating therefrom,
said processing means having a computer for receiving said electrical signal and determining coating thickness,
positioning means for effecting relative movement between said detection means and said metal object to permit sequential inspection of a plurality of sections of said coating,
a detector housing within which said first and second detectors and disposed,
said detector housing having an entry end through which said fluorescent light from said coating enters, and
lens means and filter means disposed between said entry end and said first and second detectors.

26. A method of nondestructively determining coating thickness on a surface of a metal object comprising:
providing object securing means for supporting said object during inspection, and inspection means having light source means for causing a light beam to impinge on a first section of said object and detector means for receiving light created in the coating by the beam of impinging light and returned from said surface section,
directing a beam of light onto a first section of said metal object,
delivering light created in said coating responsive to said impinging light from said first section to said detector means,
employing fluorescent light as the delivered light,
determining the thickness of said coating from said delivered fluorescent light while substantially eliminating light emitted from sources other than said first section including scatter light and ambient light, and compensating for surface irregularities in said first section of said metal in making the thickness determination.

27. The method of claim 26 including:
subsequent to inspecting said first section inspecting other sections of said surface.

28. The method of claim 27 including:
inspecting the interior of a can.

29. The method of claim 28 including:
inspecting both the curved can sidewall and the can end wall.

30. The method of claim 29 including:
employing laser light as the directed beam of light.

31. The method of claim 29 including:
said inspection means having probe means and means for effecting relative axial translational movement of said can and said probe means while inspecting a first portion of the sidewall of said can.

32. The method of claim 31 including:
subsequent to inspecting said sidewall effecting translational movement of said can in a direction perpendicular to the longitudinal axis of said can while inspecting a portion of the end wall of said can, and subsequently withdrawing said can from said probe means.

33. The method of claim 32 including:

subsequent to inspection of said sidewall and end wall retracing the path of relative can and probe means movement to restore the original position at the initiation of sidewall inspection and effecting axial rotation of said can and inspecting a different portion of said sidewall and said end wall.

34. The method of claim 33 including:

effecting each said sidewall inspection and end wall inspection along a generally linear path, inspecting said sidewall in a longitudinal direction, and effecting said end wall inspection in a generally radial direction.

35. The method of claim 26 including:

inspecting a coated generally flat metal sheet, effecting said inspection while said metal sheet is moving by said detector means, and positioning said light source means upstream with respect to the direction of sheet movement and upstream of said detector means.

36. A method of nondestructively determining coating thickness on a surface of a metal object comprising:

providing object securing means for supporting said object during inspection, and inspection means having light source means for causing a light beam to impinge on a first section of said object and detector means for receiving light created in the coating by the impinging light returned from said first section, providing in said detector means a first detector and second detector, directing a beam of light onto said first section of said metal object, delivering light created in said coating responsive to said impinging light from said first section to said detector means, delivering to said first detector fluorescent light, ambient light and scatter light, delivering to said second detector ambient light and scatter light, determining the thickness of said coating from the delivered light while substantially eliminating light emitted from sources other than said first section, compensating for surface irregularities in said first section of said metal object in making the thickness determination, emitting electrical signals from each detector corresponding to the light received by each detector, subtracting said electrical signals to provide a signal corresponding to coating thickness, inspecting a coated generally flat metal sheet, performing said inspection while said metal sheet is moving by said detector means, and positioning said light source means upstream with respect to the direction of sheet movement and upstream of said detector means.

37. The method of claim 36 including:

delivering subtracted signal to computer means and determining the thickness of said coating by said computer means.

38. The method of claim 37 including:

inspecting a coating of a naturally fluorescing material or a material to which a fluorescing tag has been added.

39. The method of claim 37 including:

inspecting a coating selected from the group consisting of an epoxy coating and dioctyl sebacate coatings.

40. A can holder comprising:

a pair of end rings having openings therein for passage of a portion of a can therethrough, a plurality of elongated struts secured to said end rings, and a plurality of radially spring biased fingers projecting inwardly from said end rings into the openings therefor, and said fingers being circumferentially spaced from adjacent said fingers on the same end ring.

* * * * *